(12) United States Patent
Eklund et al.

(10) Patent No.: US 10,209,215 B2
(45) Date of Patent: Feb. 19, 2019

(54) INTEGRATED CIRCUIT SENSOR DEVICE FOR CHARGE DETECTION HYBRIDIZING A LATERAL METAL OXIDE SEMICONDUCTOR FIELD EFFECT TRANSISTOR (MOSFET) AND A VERTICAL BIPOLAR JUNCTION TRANSISTOR (BJT)

(71) Applicant: K.EKLUND INNOVATION, Uppsala (SE)

(72) Inventors: Klas-Hakan Eklund, Uppsala (SE); Shili Zhang, Stockholm (SE); Ulf Smith, Huddinge (SE); Hans Erik Norstrom, Solna (SE)

(73) Assignee: K.EKLUND INNOVATION, Uppsala (SE)

( * ) Notice: Subject to any disclaimer, the term of this patent is extended or adjusted under 35 U.S.C. 154(b) by 0 days.

(21) Appl. No.: 14/899,428

(22) PCT Filed: Jun. 17, 2014

(86) PCT No.: PCT/SE2014/050743
§ 371 (c)(1),
(2) Date: Dec. 17, 2015

(87) PCT Pub. No.: WO2014/204394
PCT Pub. Date: Dec. 24, 2014

(65) Prior Publication Data
US 2016/0153932 A1    Jun. 2, 2016

Related U.S. Application Data

(60) Provisional application No. 61/837,383, filed on Jun. 20, 2013.

(51) Int. Cl.
*H01L 27/06* (2006.01)
*G01N 27/414* (2006.01)

(52) U.S. Cl.
CPC ....... *G01N 27/4145* (2013.01); *G01N 27/414* (2013.01); *H01L 27/0623* (2013.01)

(58) Field of Classification Search
CPC ................ H01L 27/0623; H01L 29/7371
(Continued)

(56) References Cited

U.S. PATENT DOCUMENTS

| 4,901,127 A | 2/1990 | Chow et al. |
| 5,126,806 A | 6/1992 | Sakurai et al. |

(Continued)

FOREIGN PATENT DOCUMENTS

| EP | 0178649 | 4/1986 |
| EP | 0 372 391 A2 | 6/1990 |

OTHER PUBLICATIONS

International Search Report, dated Oct. 21, 2014, from corresponding PCT Application.
(Continued)

*Primary Examiner* — Andrew Q Tran
(74) *Attorney, Agent, or Firm* — Young & Thompson

(57) ABSTRACT

A semiconductor based integrated sensor device includes: a lateral insulating-gate field effect transistor (MOSFET) connected in series to the base of a vertical bipolar junction transistor (BJT) wherein the drain-drift-region of the MOSFET is part of the base-region of the BJT within the semiconductor substrate thus making electrical contact to the base of the BJT and the distance of the drain-drift-region of the MOSFET to the emitter of the BJT exceeds the vertical distance between the emitter and any buried layer, serving as collector, and the breakdown voltage of the device being determined by the $BV_{CEO}$ of the vertical BJT.

18 Claims, 6 Drawing Sheets

(58) Field of Classification Search
USPC .......... 257/47, 197, 205, 253, 273, 370, 378
See application file for complete search history.

(56) References Cited

U.S. PATENT DOCUMENTS

| | | | | |
|---|---|---|---|---|
| 5,594,683 | A * | 1/1997 | Chen | G11C 11/40 257/273 |
| 5,717,241 | A * | 2/1998 | Malhi | H01L 27/0722 257/273 |
| 5,879,967 | A * | 3/1999 | Kim | H01L 29/66333 257/E21.383 |
| 8,283,736 | B2 | 10/2012 | Kang et al. | |
| 2011/0057230 | A1 | 3/2011 | Udrea et al. | |
| 2011/0204455 | A1 | 8/2011 | Kang et al. | |
| 2012/0181576 | A1 | 7/2012 | Lin et al. | |
| 2013/0341734 | A1 * | 12/2013 | Merz | G01N 27/26 257/414 |

OTHER PUBLICATIONS

Elizabeth Kho Ching Tee et al: A Review of techniques used in Lateral Insulated Gate Bipolar Transistor (LIGBT). IOSR Journal of Electrical and Electronics Engineering (IOSR-JEEE, No. 1, 2012, pp. 35-52, abstract, sec II.

Campos, F. S et al.: Photodetection With Gate-Controlled Lateral BJTs From Standard CMOS Technology. Sensors Journal, IEEE, vol. 13, No. 5, 2013, pp. 1554-1563; abstract; figure 1; sec II.

Yuan, H. et al: MOSFET-BJT hybrid mode of the gated lateral bipolar junction transistor for C-reactive protein detection. Biosensors and Bioelectronics, Oct. 15, 2011, vol. 28, No. 1, pp. 434-437; abstract; figure 1.

Extended European Search Report dated Jan. 27, 2017; Application No. 14813230.1.

Yuan et al., "Highly sensitive ion sensor based on the MOSFET-BJT hybrid mode of a gated lateral BJT", Sensors and Actuators B: Chemical: International Journal Devoted to Research and Development of Physical and Chemical Transducers, vol. 181, Feb. 7, 2013, pp. 44-49, XP055336045.

* cited by examiner

INTEGRATED CIRCUIT SENSOR DEVICE FOR CHARGE DETECTION HYBRIDIZING A LATERAL METAL OXIDE SEMICONDUCTOR FIELD EFFECT TRANSISTOR (MOSFET) AND A VERTICAL BIPOLAR JUNCTION TRANSISTOR (BJT)

TECHNICAL FIELD

The present invention relates to an integrated sensor device. In particular, the present invention relates to a hybrid form of semiconductor devices combining a field effect transistor with a bipolar junction transistor, the field effect transistor being connected to a sensing electrode by a plurality of contacts/vias and metal layers.

BACKGROUND OF THE INVENTION

Over the recent years a growing interest has been seen in the area of highly sensitive semiconductor devices that can be used for charge detection in liquids (e.g. ion sensitive field-effect transistor (ISFET)-type for hydrogen ions, as applied in the determination of pH-concentrations, detection of biomolecules, studies of DNA replication and genome sequences, etc.), or for the detection of ions or polarisable molecules in gaseous mixtures. Hybrid forms of such semiconductor devices have previously been proposed and demonstrated (S-R. Chang et al. Sensors 9, 2009, pp. 8336-8348 and H. Yuan et al. Biosensors and Bioelectronics 28, 2011, pp. 434-437), Ref. 1-2. These hybrids combine in a single integrated circuit an ISFET charge-sensitive device in parallel with a lateral bipolar junction transistor (LBJT). Such hybrid devices beneficially combine the high sensitivity of the ISFET with the additional amplification provided by the LBJT.

The term "ISFET" employed herein includes various equivalent forms of such devices (P. Bergveld, Sensors and Actuators B 88, 2003, pp. 1-20), see also Ref. 3-6. For example, the conductive gate electrode may be of metal or other suitable conductive material such as highly doped polycrystalline silicon. Similarly, the gate insulating material may be an oxide, such as silicon dioxide, but may as well comprise oxynitride or even high-k dielectrics.

Arrangements are known where the gate-electrode is brought in contact with the gas or liquid to be analysed via a consecutive arrangement of contacts/metal-lines and vias/metal-lines encapsulated by suitable passivation materials, as for example silicon oxide, silicon nitride or a sandwich of oxide/nitride. The metal film in the electrode in closest proximity to the liquid or gas may or may not be enclosed by said passivation. The metal itself may be a standard metal used in the manufacturing of semiconductor devices, such as aluminium, palladium, platinum or gold. The electrode may alternatively be in some form of metal/metal-oxide ($Al_2O_3$, $Ta_2O_5$, $HfO_2$).

Disclosed in U.S. Pat. No. 8,283,736 is an ion sensing device constituting an ISFET connected to a lateral bipolar device integrated on same semiconductor chip. As disclosed, a p-channel ISFET, is located in an n-well with a lateral pnp bipolar transistor connected in parallel with emitter/source and drain/collector, respectively, in common and with a separate base connection. When an appropriate amount of ions are accumulated (or depleted) at the gate electrode, as a result of bias applied to the reference electrode immersed in the electrolyte, the channel conduction in the ISFET is altered. That, in turn, affects the conduction of the lateral bipolar device.

A drawback of this particular architecture is the parallel arrangement of the two devices, which requires an additional terminal. To this comes the inherently low gain of the gated lateral bipolar transistor. At a bias lower than the turn-on voltage of the bipolar device, the sub-threshold characteristics resemble those of the metal-oxide-semiconductor field-effect transistor (MOSFET) device, i.e. ISFET in this context. The transconductance enhancement obtained in the hybrid configuration primarily occurs above the threshold voltage of the MOSFET. As a consequence, the amplification of this structure will be very low.

The parasitic vertical pnp-transistor indicated in the referenced patent, is common to all n-well based CMOS processes. It is formed by the source/emitter of the ISFET, the externally connected n-well base with the p-type substrate as collector. It is not part of the sensing device, since a conductivity change in the ISFET does not influence said parasitic component. Active use of the parasitic vertical pnp-transistor could eventually cause reliability problems, e.g. latch-up. A further concern is the requirement of additional terminals for external connection of the individual devices in the desired configuration. Such additional wiring is likely to introduce unwanted signal noise.

U.S. Pat. No. 5,126,806 describes a lateral insulated gate bipolar transistor (IGBT), which is particularly well suited for high power switching applications. Disclosed is an enhancement-MOSFET device having its source and drain electrodes connected to the base and emitter, respectively, of a lateral bipolar transistor. When an appropriate gate input voltage, here in the form of a positive charge, is applied to the MOSFET, the channel conducts, thus biasing the bipolar transistor into conduction. The applied charge on the gate electrode can be used to control a large current through the bipolar device, which is of particular interest in power applications. Safe switching operation at high voltages, however, requires a very wide base and a low gain in the bipolar transistor. Various forms of said devices have been integrated in modern CMOS processes as described by Bakeroot et al. in IEEE EDL-28, pp. 416-418, 2007, Ref. 7. Relevant in this context is also a report by E. Kho Ching Tee entitled "A review of techniques used in Lateral Insulated Gate Bipolar Transistor (LIGBT)" in Journal of Electrical and Electronics Engineering, vol. 3, pp. 35-52, 2012, Ref. 8. While this type of device is potentially quite useful for various forms of power switching, with its requirements of high voltage capability and low internal gain, it is disadvantageous for a device incorporated in a circuit intended for charge detection (of particularly hydrogen ions) in liquids or gaseous mixtures.

A prior-art ISFET-gated LBJT is described with reference to FIGS. 1A and 1B. Referring first to FIG. 1A, there is depicted a side view of the prior art device 10 representative of a device disclosed in the above cited U.S. Pat. No. 8,283,736. As shown in the Figure, the gated LBJT 10 is constructed by forming an n-well 12 in a p-type substrate 11, forming p+-doped regions in the n-well 12 and forming a lateral collector ring 15 around an emitter 13 in the p+-doped regions, respectively.

The gated LBJT 10 has an enclosed gate electrode 18, between p+-doped regions, on top of a gate dielectric layer 17. In addition, a base contact 14 is formed in an n+-doped region in the n-well 12. Likewise, a p+-doped region 16, outside the n-well is provided as substrate contact.

The gate electrode 18 and the p+-doped regions on adjacent sides, which function as source/drain contacts, constitute a p-type MOSFET device.

The floating gate electrode 18 is electrically connected by a plurality of contacts/vias and metal layers 21 to a hydrogen ion sensing electrode 19 above the gated LBJT. The surface of the sensing electrode 19 is in contact with an ion-containing solution 22 to which a reference gate-electrode 20 is attached.

In the prior art of FIG. 1A, the MOSFET drain region and the bipolar transistor collector region are inherently connected because they are formed from the same p+-conductivity type semiconductor region.

The MOSFET source region and the bipolar emitter region are likewise connected since they are formed by the same p+-type semiconductor region 13. In the particular structure depicted in FIG. 1A, an n+-region 14 is made in the n-well 12 for a common external bias connection to the base region of the bipolar lateral and vertical pnp transistors as well as to the body of the p-type MOSFET (ISFET).

Referring now to FIG. 1B, which is the equivalent circuit for the device in FIG. 1A, it can be seen that there are four terminals; B 14, C 15, E 13, S 16 in addition to that of the external reference gate-electrode, Ref 20. It can be seen that the p-type MOSFET has its source 13 and drain 15 terminals connected in parallel to the emitter (E) and collector (C) of the lateral bipolar device 5. It is similarly observed that both the lateral pnp-transistor and the vertical (parasitic) pnp-transistor 6 share emitter (E) and base (B) terminals.

Applying proper bias to the source/drain terminals of the MOSFET and to the reference electrode will result in a lateral current in the MOSFET device.

Forward biasing of the emitter-base junction will add a lateral current, which is picked up by the lateral collector ring (15) in FIG. 1A and will also add a vertical substrate current that will be globally distributed in the substrate (11) in FIG. 1A.

Any change in the reference potential will affect both the MOSFET current as well as the current passing through the bipolar device(s).

For the described prior art device, any change of potential or charge in the electrolyte part is primarily sensed by the parallel arrangement 5 of the MOSFET transistor and the lateral pnp-bipolar transistor.

The fact that the active layers are shared between the p-type MOSFET and the lateral pnp-transistor, respectively, leads to a non-optimised low current-gain pnp-transistor.

In addition, the substrate current from the vertical parasitic pnp-transistor 6 is disadvantageous from a device isolation point and does not provide information with respect to changes in the electrolyte part.

FIG. 2A shows one example of prior art in the form of LIGBT such as described in U.S. Pat. No. 5,126,806 mentioned above. The integrated device 30 is constructed in a low-doped n-type layer 35 containing a p-type doped region 50 with a higher impurity concentration than that of the n-type layer and a p+ region 70 with an impurity concentration exceeding that of the p-type doped region 50. In the p-doped region 50 is provided an n+-region 60 with an impurity concentration that is higher than that of the p-type region 50. The p-doped region 50 and the n+-region 60 are electrically short-circuited by an emitter electrode 55. A collector electrode 65 forms an ohmic contact to the p+-region 70. An insulating film serves as gate dielectric 40 and separates the gate electrode 45 from the substrate.

When a positive potential is applied to the gate electrode 45, the conductivity of a surface portion of the p-region 50 under the gate dielectric 40 is inverted to form an n-type channel. Electrons from the n+-region 60 can then pass through the channel, into the n− layer 35 and on to the p+-region 70 from which positive holes are injected. Thereby the n− layer 35, having a high resistivity, is conductivity-modulated to provide a low resistance path between the anode (C) and cathode (E) in FIG. 2A. A low on-resistance and excellent forward blocking characteristic can thus be realised, which is quite useful for various forms of power switching.

Numerous modifications of the above described embodiment, with emphasis on improved switching performance, exist, some of which are covered in a report by E. Kho Ching Tee, Ref. 8.

FIG. 2B, is an equivalent electrical circuit diagram for the device in FIG. 2A. Shown are the three terminals, C, E and G. The device also utilises an external back-side substrate electrode. The n-type MOSFET has its source and body terminals strapped together at (E) and these are, in turn, connected to the collector region (C) of the lateral bipolar pnp-transistor over the body resistance, R1. Shown is also how the base terminal of the lateral pnp-transistor is connected to the drain of the MOSFET over a variable resistance, R2, the latter mirroring the conductivity modulation.

A vertical parasitic npn-transistor that has its base connected to the collector of the lateral pnp-transistor is included in FIG. 2B to illustrate that the LIGBT contains a thyristor-like structure. Once this thyristor causes latch-up, the LIGBT device can no longer be controlled by the gate potential. The condition for latch-up is: $\alpha_{npn}+\alpha_{pnp} \geq 1$, where $\alpha_{npn}$ and $\alpha_{pnp}$ are the common-base current gains of the parasitic npn transistor and pnp transistor, respectively. To reduce the risk for latch-up, it is essential to lower the current gain $\alpha$ in both transistors. Since the pnp transistor carries the on-state voltage drop, the gain of the npn-transistor has to be suppressed by, e.g., increasing the base doping below the emitter region (lowering the base resistance).

SUMMARY OF THE INVENTION

Obviously, an improved sensor device based on hybrid form of semiconductor devices combining a field effect transistor with a bipolar junction transistor is needed, with reference to FIGS. 3 through 7.

The object of the present invention is to provide a highly sensitive integrated sensor device, with internal amplification, that can be used for charge detection in liquids or for the detection of ions or polarisable molecules in gaseous mixtures. This is achieved by the device as disclosed below and as recited in the claims of the instant application.

The instant invention herein described provides a floating gate MOSFET intimately merged with a vertical bipolar junction transistor, BJT, characterised by having a very high internal amplification, a high signal-to-noise ratio, and operating at low supply voltages. In the preferred embodiment, the device can be realised in a standard low-voltage CMOS process as provided by semiconductor foundries worldwide.

The integrated sensor according to the present invention comprises a lateral Metal Oxide Semiconductor Field Effect Transistor (MOSFET) and a Bipolar Junction Transistor (BJT) arranged in a semiconductor substrate, wherein the MOSFET is connected in series to the base of the vertical BJT. The MOSFET is arranged to be connected at the semiconductor substrate surface, and the emitter of the BJT is located at the semiconductor substrate surface. The drain-drift region of the MOSFET is part of the base-region of the BJT within the semiconductor substrate, the drain-drift region thus making electrical contact to the base of the BJT. The distance from the drain-drift region of the MOSFET to the emitter of the BJT exceeds the vertical distance between the emitter and any buried layer serving as collector. Hence, the breakdown voltage of the device is determined by the $BV_{CEO}$ of the vertical BJT.

The sensor device according to a particular embodiment of the invention further comprises an ion-sensitive electrode, electrically connected by a plurality of contacts/vias and metal layer(s) to the floating gate-electrode. The surface of the ion-sensing electrode is in contact with an ion-containing solution to which a reference gate-electrode is attached, wherein electrodes are arranged in ohmic contact with a third region in contact with the buried layer serving as collector of the BJT, a fourth region serving as an emitter of the BJT, a fifth region serving as the source of the MOSFET, and a sixth region providing ohmic contact to the third region regions for the purpose of external device connection and signal extraction.

The integrated sensor device according to a particularly preferred embodiment comprises:
  a semiconductor substrate of a first doping type;
  a first region of a second doping type, functioning as a buried layer for the device within said substrate and located below the substrate surface, said region constituting a right-angled polygon as seen in the plane of the substrate;
  a second region of a first doping type, serving as base of the BJT and drain-drift-region of the MOSFET, and extending from the substrate surface and vertically a distance into said substrate to make contact to and create a semiconductor junction with the buried layer of second doping type in said substrate, said region constituting a right-angled polygon as seen in the plane of the substrate;
  a third region of a second doping type that surrounds and encloses said second region of first doping type and extends from the substrate surface vertically a distance into said substrate to make an electrical contact to the buried layer of second doping type and providing said region with at least one ohmic contact at the surface, said region constituting a right-angled polygon as seen in the plane of the substrate;
  a dielectric film on said substrate surfaces of said second and third regions and over said regions, forming at least one gate-electrode in the form of a rectangular conducting stripe on said dielectric film, said stripe overlapping the interface between said second and third regions and extending into parts of said second and third regions, said gate-electrode stripe in the plane of the substrate running along the interface between the second and third regions;
  at least one fourth region, in the form of a right-angled polygon of a second conductivity type extending from a surface and into and inside said second region serving as emitter of the BJT, said fourth region being in the horizontal plane parallel with the interface between second and third regions;
  a fifth region of said first conductivity type, extending from a surface of and into said third region that is adjacent to and slightly overlapped by the rectangular gate-electrode stripe, serving as source of the MOSFET, said region of first conductivity type being in the plane of the substrate located on the side away from the intersection of said second and third regions, said region of said first conductivity type being juxtaposed and slightly covered by said rectangular gate-electrode stripe, said region constituting a right-angled polygon as seen in the plane of the substrate;
  a sixth region of said second conductivity type, extending from a surface and into said third region of second conductivity type and providing ohmic contact to said third region, said region of second conductivity type being in the plane of the substrate located away from the gate electrode stripe and the second region of first conductivity type; and
  a seventh region of said first conductivity type extending into a section of said second region thereby providing a low-resistivity region serving as drain-drift region of the MOSFET, said seventh region being adjacent to and overlapped by said rectangular gate-electrode stripe in said second region, said seventh region being in the plane of the substrate juxtaposed and slightly covered by said rectangular gate-electrode stripe, wherein said region simultaneously serves as drain-drift-region of the MOSFET and base to the BJT, thereby providing a low resistivity supply path for the base current.

According to an embodiment of the invention, an MOSFET is provided, with its drain connected in common to the extrinsic base of a vertical BJT as described above, wherein the MOSFET is of n-type and said BJT is of pnp-type.

The integrated sensor according to the present invention has a broad range of applications at the molecular level, such as, but not limited to, medical diagnostics devices, environmental and bioprocess analysis devices and food processing and chemical process monitoring devices.

Areas of application should however not be limited to those listed above since it is obvious to those skilled in the art that the proposed device, without an ion sensing electrode, can be used as an amplifier in many types of electronic circuits.

One advantage of the present invention is that the sensor device can be built from methods and means that are well-established within the microelectronics field. The manufacturing costs will therefore correspond to what is to be expected for standard integrated circuits. Furthermore, the design only has such features that make sensing chips consisting of a multitude of said MOSFET/BJT devices easily manufacturable at facilities already commercially available.

A maximum signal-to-noise output can only be obtained if amplification is applied as close to the signal source as possible. In the present invention this is achieved automatically by way of the first amplification stage being merged with the sensor itself.

The high gain and excellent signal-to-noise properties of the present invention obviate the need for heretofore costly sample enrichments by providing sensing chips for which the manufacturing costs are still held at the low level typical of IC manufacturing.

BRIEF DESCRIPTION OF THE DRAWINGS

The invention will now be described in detail with reference to the drawing figures, wherein.

DETAILED DESCRIPTION OF THE PREFERRED EMBODIMENTS

Figure 1A:
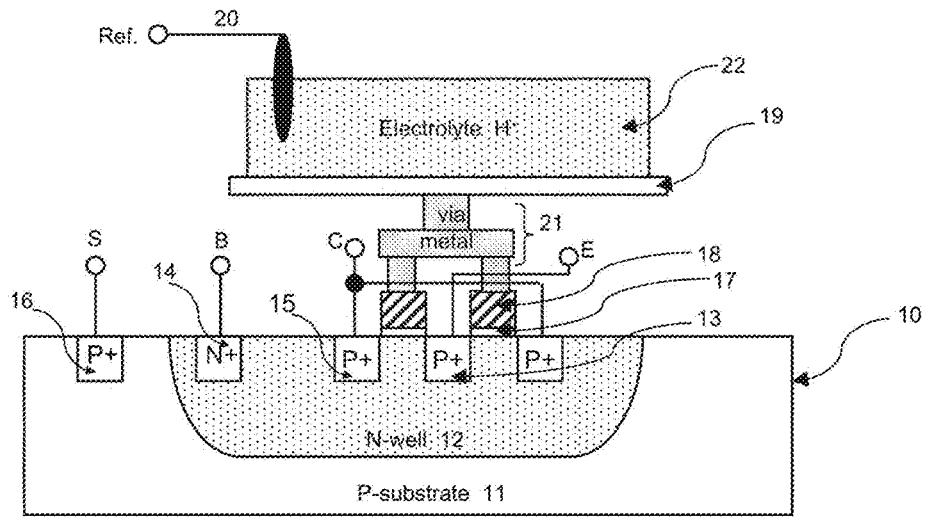
FIG. 1A is a sectional view illustrating a hydrogen ion sensing device with a gated lateral bipolar transistor according to prior art, and 1B is the equivalent circuit diagram of the prior-art device in FIG. 1A.
Figure 1B:
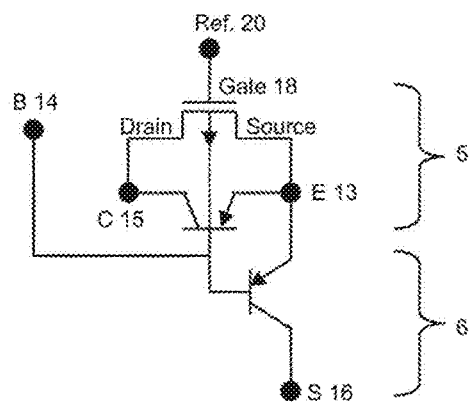
Figure 2A:
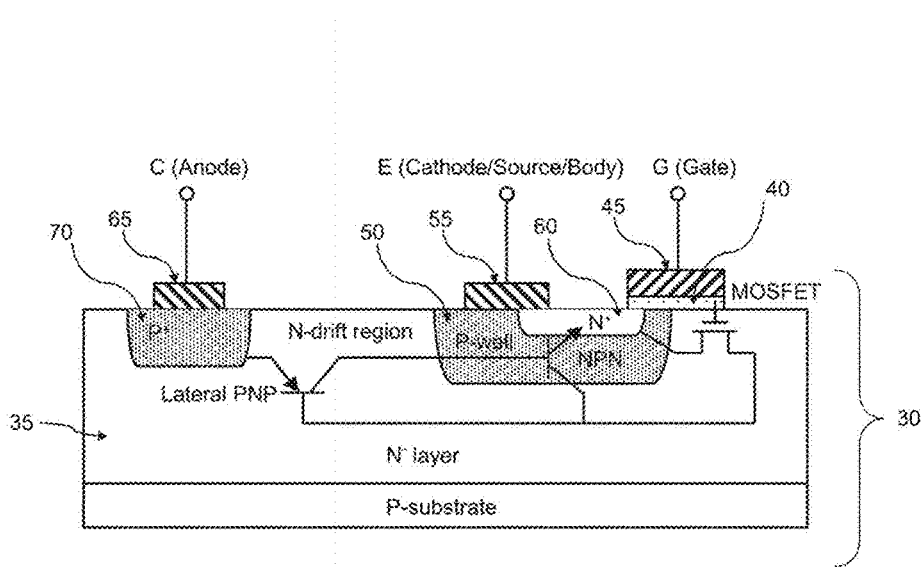
FIG. 2A is a sectional side view depicting a representative prior art lateral insulated gate bipolar transistor (LIGBT), and 2B is the equivalent circuit of the prior-art device in FIG. 2A.
Figure 2B:
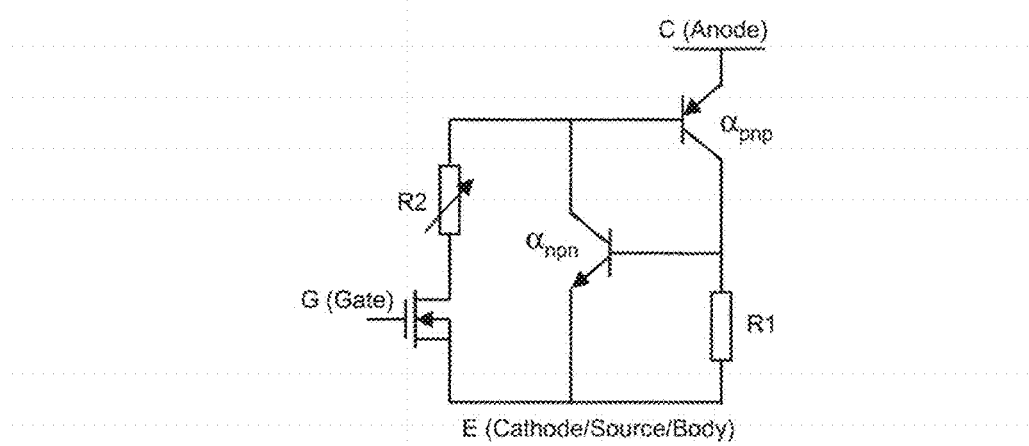
Figure 3:
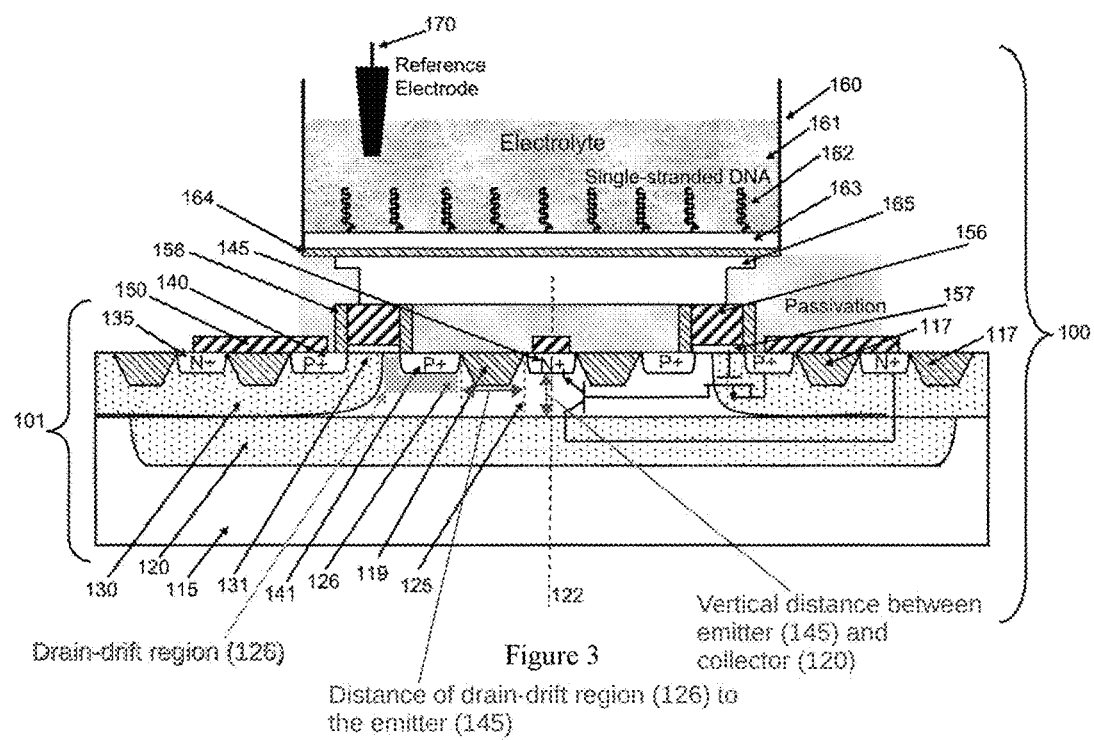
FIG. 3 illustrates schematically the structure of a first embodiment of the electronic sensor according to the present invention.

The function of the floating gate structure can be illustrated by the following application example, where DNA strands of a known base-sequence are immobilized to a desired surface density on the bottom metal surface of the electrolyte vessel in FIG. 3. The vessel is connected to a flow cell for a programmed sequential supply of the four nucleotides (nucleobases) A, C, G and T, not necessarily in this order but with one type at a time. Every time when base-paring (i.e. A-T or C-G bindings) occurs between the DNA strands and the incoming nucleotides, a large number of protons are released. This causes an instantaneous change in the pH value in the electrolyte. This, in turn, induces protonation of the bottom surface of the vessel. This protonation induces a change of the surface potential which is transmitted to the gate via the sandwiched metal layers. At the gate, the change induces a change in the current flowing between the source and drain terminals and into the base of the bipolar transistor. In order to maximise sensitivity, the bottom surface of the vessel can be coated with an appropriate layer, typically a metal oxide that is especially sensitive to protonation and de-protonation.

The type and shape of the electrolyte vessel shown in the Figures is only intended as an example, the electrode in the bottom of the vessel and its role in gating the MOSFET being the important aspects for the current context. Actual forms of the sensing part are intimately related to respective applications and clear to those versed in respective fields. Furthermore, it should be clear to those versed in the field of semiconductor technology that the electrolyte vessel and/or any individual compartment(s) holding the molecules in place above the sensing element(s) can be designed with dimensions in a range from macro to micro. Practical limits in the micro range are set by the design requirements arising from the state-of-the-art of semiconductor manufacturing technology. One consequence of this is that the vessel-sensor assembly can be repeated in amounts numbering millions on a single semiconductor chip. The Reference Electrode can also be designed in a multitude of ways, as known by those versed in the field. In one example, relevant to the present invention, a silver film is placed on the surface of the semiconductor chip itself and appropriately converted to silver chloride. In this context, it is worth noticing that the floating extended gate structure in FIG. 3 serves yet another purpose in that the construction prevents the fluid from attacking the transistor electronics chemically. This protection makes it possible to include the control electronics on the same semiconductor chip as the sensor assembly, an arrangement which not only preserves signal integrity, but also permits sensor designs small enough to fit into, for example, Point-Of-Care applications.

Figure 6:
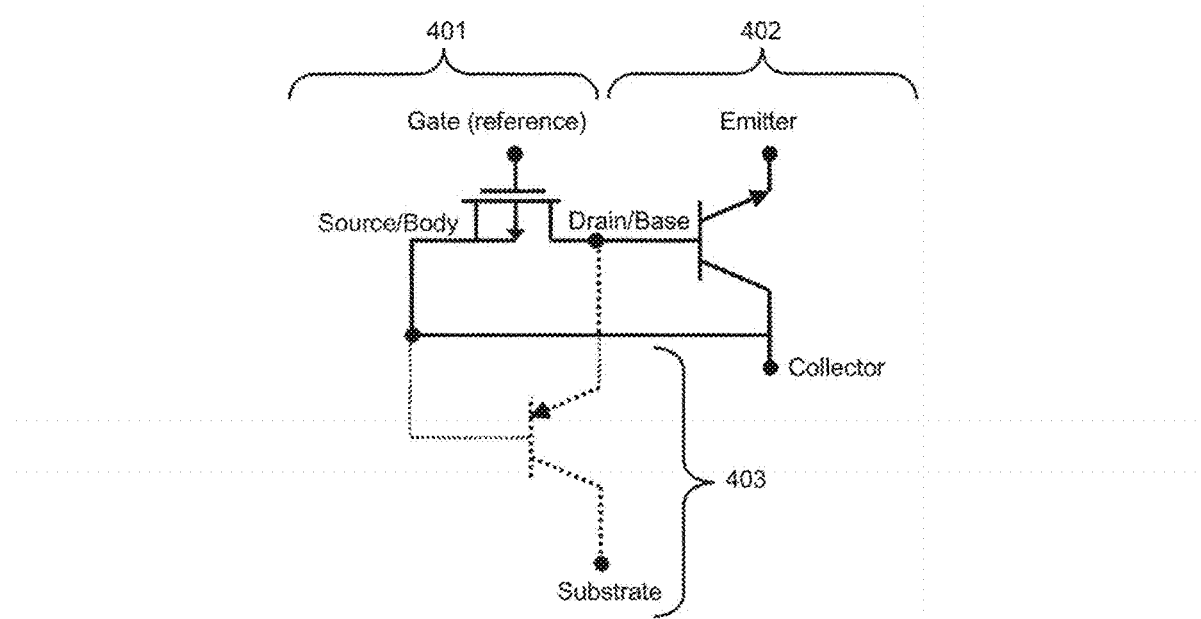
FIG. 6 is the equivalent circuit scheme of the electronic sensor according to the present innovation.

The functionality of the inventive device is outlined with references to FIGS. 3 and 6. The device is put into operational mode by biasing the MOSFET source and n-well (strapped together) positive with respect to ground. Since the collector is internally connected to the n-well, the collector will likewise receive a positive bias with respect to the emitter which is kept at ground potential. The potential of the Reference (Gate) Electrode, with respect to ground, can be selected so as to determine the operational mode of the MOSFET device (e.g., sub-threshold region or saturation region). During operation, the resulting current at the (metal strapped) collector terminal is measured. This current, which is the sum of the MOSFET channel current and the current passing through the BJT, is influenced by the density of DNA molecules and electric charges related thereto that are present on the electrode surface immersed in the electrolyte. This influence expresses itself due to the fact that the field in the MOSFET channel is capacitively coupled to the potential difference between the reference electrode and the MOSFET source (see, e.g., FIG. 3).

The electronic sensor according to the present invention can be adapted for detecting various charged and/or polarized substances in a variety of applications, examples including, but not being limited to, the liquid detection of ions (e.g., H+, Na+, and Ca++) for biomedical and food quality monitoring applications, detection of biomolecules by the arrangement outlined above, as well as gas monitoring applications. For the latter, a sample vessel is not a necessity, but surface functionalisation is still a key step in order to attain selectivity and specificity in sensing.

The emitter, base and collector of the vertical BJT, that is part of the sensor device, are built up by means of a vertical stacking of laterally extending doped layers on a semiconductor substrate. The base layer of the BJT has a vertically extending portion that reaches the surface next to the emitter and forms the drain of the laterally-oriented MOSFET. Proceeding along the surface, the drain is followed by the channel and the source regions of the MOSFET. The collector region of the vertical BJT is located below the base region, where it forms a lateral band. The collector is of a conductivity-type opposite to that of both the base and the substrate so as to form the necessary junctions. Above, and in direct contact with, outer parts of the lateral collector band is a well of a same conductivity type. The well is thus adjacent to the base region and extends laterally along the surface so as to allow for a connection to the collector region.

Preferably, the device is constructed in such a way that it has mirror symmetry, vis-à-vis an imaginary vertical plane passing through the emitter region of the BJT and perpendicular to the plane of the paper, thereby providing a double combined MOSFET/BJT.

In FIG. 3, there is illustrated, in accordance with one embodiment of the invention, an integrated sensor device consisting of a floating base composite BJT-MOSFET charge-sensitive device 101, electrically connected to a sample vessel 160.

The integrated sensor device 100 in FIG. 3 thus comprises a combined MOSFET and BJT, as indicated by the overlaid schematic circuit drawing in the Figure.

Starting from the bottom in FIG. 3, the device comprises a p-type silicon substrate 115 of types well known in the field. Said substrate 115 is preferably of (100)-orientation. Substrate 115 can also, in an embodiment of the invention, be a Silicon-On-Insulator (SOI) substrate. Within part of the substrate 115, a vertical npn-transistor, i.e. a BJT, is formed by a first buried n-type region 120, referred to, as the n-band, with a typical thickness in the order of 1 μm and a typical dopant concentration in the range of $1 \cdot 10^{17}$ to $1 \cdot 10^{19}$ cm$^{-3}$, followed by a p-region 125 forming a p-well and with a typical thickness in the order of 1 µm and a typical dopant concentration in the range of $1 \cdot 10^{17}$ to $1 \cdot 10^{18}$ cm$^{-3}$, and an n$^+$-region 145 with a typical concentration in the range of $1 \cdot 10^{19}$ to $1 \cdot 10^{20}$ cm$^{-3}$. The n$^+$-region 145 is enclosed by the p-well 125 and extends from the surface thereinto approximately 0.2 µm.

An oxide isolation 119, stretching from the surface approximately 0.3 µm into the p-well 125, encloses the emitter region 145. Here, the p-region 125 acts as the base, the n-band 120 as the collector, and the n$^+$ region 145 as the emitter in the vertical BJT.

An n-region 130, forming an n-well, has a typical thickness in the order of 1 µm and is vertically in contact with the n-band and stretches to the surface is formed.

A gate structure, comprising a gate electrode 156, a gate oxide 157 and insulators 158, is formed on top of the surface at the border between the n-region 130 and the p-region 125. Said gate electrode 156 and gate oxide 157 stretches across the border formed by the n-region 130 and the p-region 125. The insulators 158 provide insulation from contact metal layer 150. Alternatively, the gate oxide 157 consists of another type of dielectric material, such as so-called "high-k dielectrics", for example hafnium, zirconium oxides, or silicates.

The n-region 130 extends in the lateral direction under the MOSFET, and has a portion 131 extending in the vertical direction towards the top surface of the device. The surface of the vertical portion 131 of the n-region 130 also forms the n-type doped channel region of the p-type MOSFET.

A portion 126 of the p-region 125 extends in the vertical direction towards the surface of the device from a level below that of the oxide isolation 119 until adjacent to the corresponding portion of the n-region 131. Said vertical portion 126 of the p– region 125 forms the drain-drift region of the MOSFET.

Moreover, there is provided a p$^+$-doped drain region 141, adjacent to the gate electrode 156 of the MOSFET, extending from the surface and thereinto approximately 0.2 µm with a typical surface concentration in the range of $1 \cdot 10^{19}$ to $1 \cdot 10^{20}$ cm$^{-3}$. Said p$^+$-drain region 141 is located within part of the p-region 125 serving as low ohmic shunt to a part of said drain-drift region 126.

The oxide isolation 119 that separates the p$^+$-doped drain region 141 in the p-region 125 from the n$^+$-region 145, the latter being the emitter of the BJT, will improve the characteristics of the emitter-base/drain diode. The addition of the p$^+$-doped drain region 141, being adjacent to the oxide ring, will likewise improve the base resistance and the performance of the BJT device.

At least partly enclosed by the n-region 130 is a contacting n+-region 135 extending from the surface and thereinto approximately 0.2 µm and with a typical surface concentration in the range of $1 \cdot 10^{19}$ to $1 \cdot 10^{20}$ cm$^{-3}$. The n-region 130 with its n+-doped contact region 135 serves as the body of the p-type MOSFET. The n+ contact region 135 is separated by an oxide isolation region 117, stretching from the surface approximately 0.3 µm into the n-region 130, from the p$^+$-doped source region 140 of the MOSFET. The p$^+$-source region being formed within the n-type region 130 is extending from the surface and thereinto approximately 0.2 µm and has a typical surface concentration in the range of $1 \cdot 10^{19}$ to $1 \cdot 10^{20}$ cm$^{-3}$. A metal layer 150 connects to the contact n+-region 135 as well as to the p$^+$-source region 140, thus forming a combined body/source connection.

The gate structure can connect with a sample vessel 160, adapted to hold, for example, an electrolyte 161 and functionalized bio-molecules 162. A reference electrode 170 is immersed in the electrolyte in the sample vessel 160. The sample vessel 160 may be connected to the gate 156 via a metal layer 163 at its bottom, an intermediate dielectric layer 164, e.g. a Si$_3$N$_4$-layer and one or several sandwiched metal layers 165. Alternatively, if the electronic sensor is adapted to detect, for example, gases, the sample vessel and its bottom metal layer are replaced with an appropriately functionalized surface.

As indicated in FIG. 3, the n-region 130, the oxide isolations 117, the contact n+-region 135, the p$^+$ source region 140, the metal contact layer 150, the gate electrode 156, the p$^+$ drain region 141, and the oxide isolation 119 can be mirrored vis-à-vis an imaginary vertical plane 122 that passes through the emitter region 145 and the p-region 125 and is perpendicular to the plane of the paper. This represents a non-limiting example, which may be preferred in view of functionality and manufacturing ease. It should also be noted that the device could, in another embodiment, be built in the form of an n-type MOSFET and a BJT having a pnp-configuration by means of an appropriate change of the polarity of the doping layers and substrate referred to in the description above. Furthermore, the above-given dimensions and concentrations should be seen as non-limiting examples. As is well known in the art, doping concentrations, for example, can be varied and optimized in different ways, such variations being apparent for the person skilled in the art.

Figure 4:
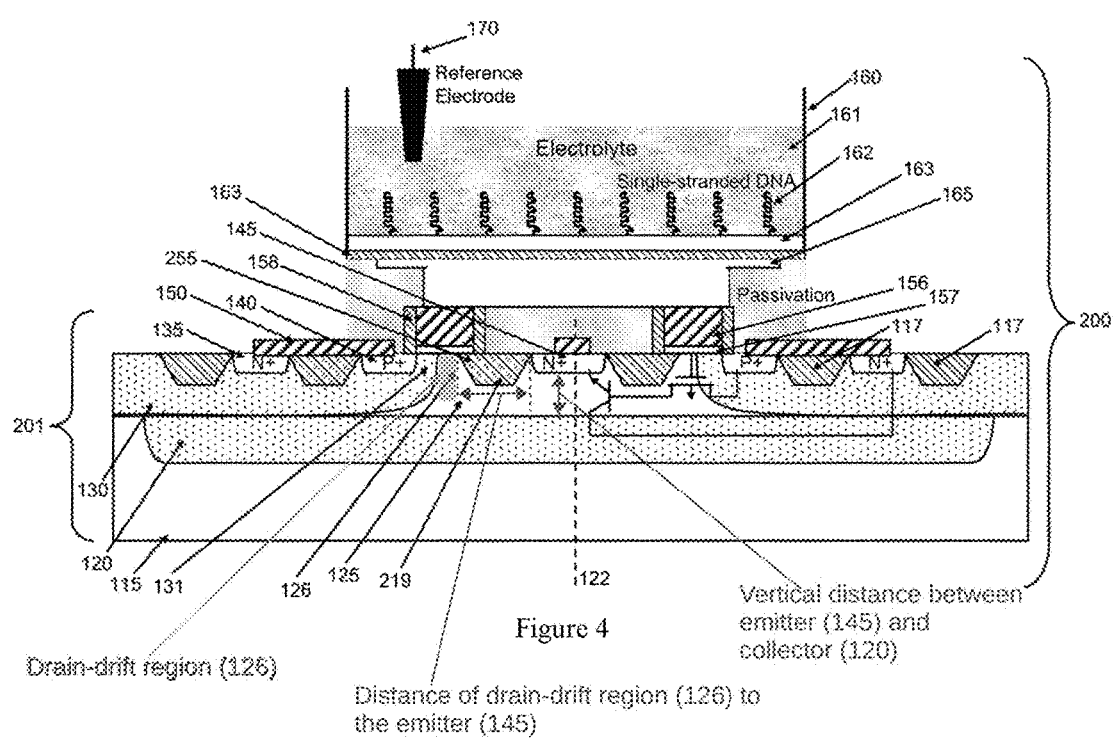
FIG. 4 illustrates schematically the structure of a second embodiment of the electronic sensor according to the present invention

In FIG. 4, is shown another embodiment of the invention. In FIG. 4 the reference numerals designate the same parts as those already shown in FIG. 3.

In general, the structure of the floating base composite BJT-MOSFET charge-sensitive devices 101 and 201 in FIGS. 3 and 4, respectively, are similar, with the important exception that, in FIG. 4, the oxide isolation 219 that separates the MOSFET drain in the p-region 125 from the n$^+$-region 145 serving as emitter of the BJT is partly over-lapped 255 by the gate electrode 156. It is similarly observed that a portion 126 of the p-region 125 extends in the vertical direction towards the top surface of the device, adjacent to the corresponding portion of the n-region 131. The vertical portion 131 of the n-region 130 forms the n-type doped channel region of the p-type MOSFET, and the vertical portion 126 of the p– region 125 forms the drain-drift-region of the MOSFET. The oxide isolation region 219 is stretching from the surface approximately 0.3 µm into the p-region 125. The p$^+$-doped drain region 141, acting as a low ohmic shunt, is omitted. This allows for a higher packing density but results in a slightly increased base-resistance.

Figure 5:
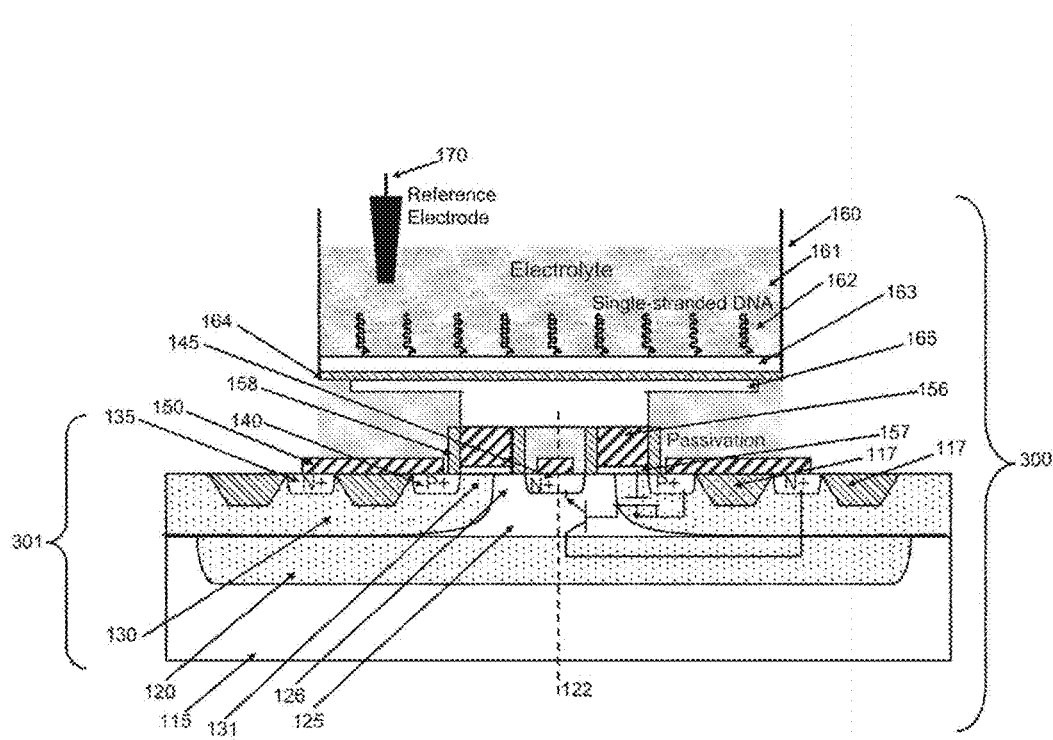
FIG. 5 illustrates schematically the structure of a third embodiment of the electronic sensor according to the present invention

In FIG. 5, is shown another embodiment of the invention. In FIG. 5, the reference numerals designate the same parts as those already referred to in FIGS. 3 and 4.

The structure of the floating base composite BJT-MOSFET charge-sensitive device 301 in FIG. 5 exhibits some important differences with respect to FIGS. 3 and 4 in that there is no oxide isolation region that separates the drain-drift region 126 of the MOSFET from the n$^+$-region 145 serving as emitter of the BJT. This results in a simple topological design that allows for densely packed structures.

Figure 7:
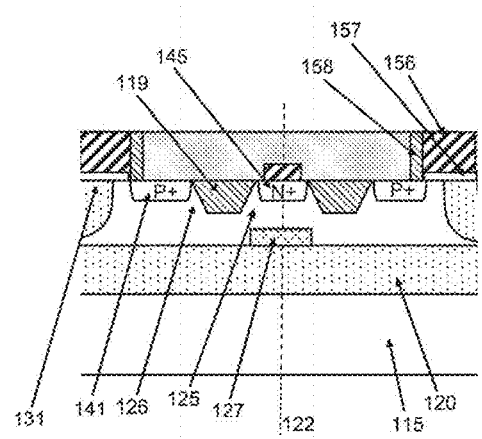
FIG. 7 illustrates schematically the structure of a part of the electronic sensor according to the present invention

An optional addition of a second n– region 127, extending from and in electrical contact with the n-band layer 120 stretching towards the emitter n$^+$-region 145, allows dopant profile tailoring and device optimization of the BJT see FIG. 7. The second n– region 127, forming a collector pedestal, is located below the p– region 125 serving as the base of the BJT and thus determines the base-width.

Referring now to FIG. 6, which is the equivalent circuit for the device in FIGS. 3, 4 and 5, respectively, it can be seen that there are three terminals in addition to that of the external reference gate-electrode. With reference to the numerals in FIGS. 3, 4 and 5, it can be seen in FIG. 6 that the p-type MOSFET 401 has its p⁺ source 140 and n+-layer 135 tied together by a metal layer 150, and that these are internally connected, via the n-region 130, to the collector 120 of the vertical npn-BJT 402. Similarly, the drain-drift-region of the MOSFET and the vertical BJT base region are inherently connected because they are part of the same p-type region 125.

The MOSFET device 401 thus appears in series with the base of the vertical npn-BJT 402, the n-type emitter region 145 of the latter being at the semiconductor surface.

It is likewise observed that a vertical (parasitic) pnp-transistor 403 is formed by the p-type region 125 serving as emitter, the n-band 120 acting as base and the p-type substrate 115 functioning as global collector. To reduce the current gain of said parasitic transistor so as to avoid latch-up, a high doping level and a large layer thickness are used in realization of the n-band.

In this configuration, the channel current generated by the MOSFET 401 is also the base current in the BJT 402. The signal on the gate can therefore, by means of the channel current, be amplified in the BJT 402 and therefore emerge from the sensor in the form of a strong collector current response at the collector terminal. By operating the p-type MOSFET 401 in the sub-threshold regime for best sensitivity and linearity, a change in the surface potential of the floating gate, as caused by, e.g., charged molecules at the bottom of sample vessel 160, will lead to a corresponding change in the amplified collector current. The operating point of the MOSFET is set by the application of a bias between the reference electrode and the source terminal of the MOSFET in FIG. 6. Since the device of the invention fuses a MOSFET and a BJT, noise entering the signal path before the signal has reached the first amplification stage is excluded.

A plurality of above described, floating base composite BJT-MOSFET charge-sensitive devices 101, 201 and 301 on same substrate 115 can be connected in parallel, each device including an ISFET directly merged to a BJT and a floating gate 156 connected via a plurality of contacts/vias and metal layers 165 to an electrode 163 in contact with the electrolyte 161, so as to improve sensitivity.

Likewise a plurality of said integrated sensor devices 101, 201 and 301 on same substrate 115 can be connected via a plurality of contacts/vias and metal layers 165 in an array configuration with each floating gate connected to an individual electrode 163 in contact with the electrolyte 161, so as to sequentially monitor the collector current of each individual integrated sensor device.

REFERENCES

[1] S.-R. Chang, H. Chen, "A CMOS-Compatible, Low-Noise ISFET Based on High Efficiency Ion-Modulated Lateral-Bipolar Conduction", Sensors 9, 8336-8348 (2009)
[2] H. Yuan, H.-C. Kwon, S.-H. Yeom, D.-H. Kwon, S.-W. Kang, "MOSFET-BJT hybrid mode of the gated lateral bipolar junction transistor for C-reactive protein detection", Biosensors and Bioelectronics 28, 434-437 (2011)
[3] J. M. Rothberg, W. Hinz, T. M. Rearick, J. Schultz, W. Mileski, M. Davey, J. H. Leamon, K. Johnson, M. J. Milgrew, M. Edwards, J. Hoon, J. F. Simons, D. Marran, J. W. Myers, J. F. Davidson, A. Branting, J. R. Nobile, B. P. Puc, D. Light, T. A. Clark, M. Huber, J. T. Branciforte, I. B. Stoner, S. E. Cawley, M. Lyons, Y. Fu, N. Homer, M. Sedova, X. Miao, B. Reed, J. Sabina, E. Feierstein, M. Schorn, M. Alanjary, E. Dimalanta, D. Dressman, R. Kasinskas, T. Sokolsky, J. A. Fidanza, E. Namsaraev, K. J. McKernan, A. Williams, G. T. Roth, J. Bustillo, "An integrated semiconductor device enabling non-optical genome sequencing", Nature 475, 348-352 (2011).
[4] Y. Cui, Q. Q. Wei, H. K. Park, C. M. Lieber, "Nanowire nanosensors for highly sensitive and selective detection of biological and chemical species", Science 293, 1289-1292 (2001).
[5] G. Zheng, F. Patolsky, Y. Cui, W. U. Wang, C. M. Lieber, "Multiplexed electrical detection of cancer markers with nanowire sensor arrays", Nat. Biotechnol. 23, 1294-1301 (2005).
[6] E. Stern, J. F. Klemic, D. A. Routenberg, P. N. Wyrembak, D. B. Turner-Evans, A. D. Hamilton, D. A. LaVan, T. M. Fahmy, M. A. Reed, "Label-free immunodetection with CMOS-compatible semiconducting nanowires", Nature 445, 519-522 (2007).
[7] B. Bakeroot, J. Doutreloigne, P. Vanmeerbeek, P. Moens, "A New Lateral-IGBT Structure with a Wider Safe Operating Area", IEEE Electron Device Letters 28, 416-418 (2007).
[8] E. K. C. Tee, A. Holke, S. J. Pilkington, D. K. Pal, N. L. Yew, W. A. W. Z. Abidin, "A Review of techniques used in Lateral Insulated Gate Bipolar Transistors (LIGBT)", IOSR Journal of Electrical and Electronics Engineering (IOSR-JEEE) 3, 35 (2012).

The invention claimed is:

1. An integrated sensor device, comprising:
   a lateral Metal Oxide Semiconductor Field Effect Transistor (MOSFET) and a vertical Bipolar Junction Transistor (BJT) arranged in a semiconductor substrate,
   wherein the MOSFET is connected in series to the base of the vertical BJT,
   wherein the MOSFET is arranged to be connected at the semiconductor substrate surface, and an emitter of the BJT is located at the semiconductor substrate surface,
   wherein a drain-drift region of said MOSFET is part of the base-region of said BJT within the semiconductor substrate, the drain-drift region thus making electrical contact to the base of the BJT, and
   wherein a lateral distance of the drain-drift region of the MOSFET to the emitter of the BJT is greater than a vertical distance between the emitter and a buried layer that operates as a collector of the BJT.

2. The integrated sensor device according to claim 1, wherein the breakdown voltage of the device being determined by the BVCEO of the vertical BJT.

3. The integrated sensor device according to claim 1, wherein the gate electrode of said MOSFET overlaps the interface between an n-region and a p-region in said semiconductor substrate.

4. The integrated sensor device according to claim 1, wherein said MOSFET in operation is biased in the sub-threshold region and the BJT is biased in the active region.

5. The integrated sensor device according to claim 1, further comprising:
   an ion-sensitive electrode electrically connected by a plurality of metal layers to a floating gate-electrode of said MOSFET,
   a surface of said ion-sensitive electrode being in contact with an ion-containing solution to which a reference gate-electrode is attached,
   wherein electrodes are arranged in ohmic contact with a collector region in contact with the buried layer serving as the collector of the BJT, an emitter region serving as the emitter of the BJT, a source region serving as a source of the MOSFET, and a connection region providing ohmic contact to the collector region for external device connection and signal extraction.

6. The integrated sensor device according to claim 5, wherein said ion-sensitive electrode consists of a metal consisting of Au, Pt, Pd and Al.

7. The integrated sensor device according to claim 5, wherein the surface of said ion-sensitive electrode is covered by tantalum oxide, aluminium oxide, silicon oxide, hafnium oxide, zirconium oxide or silicon nitride.

8. The integrated sensor device according to claim 1, wherein the integrated sensor device is mirrored vis-à-vis an imaginary vertical plane through the emitter and base of the BJT.

9. The integrated sensor device according to claim 1, wherein a plurality of said integrated sensor devices on a same substrate are electrically connected in parallel to improve sensitivity.

10. The integrated sensor device according to claim 1, wherein a plurality of said integrated sensor devices on a same substrate are electrically connected in groups, each permitting a separate sensing operation.

11. The integrated sensor device according to claim 1, wherein said MOSFET is of p-type, and said BJT is of npn-type.

12. The integrated sensor device according to claim 1, wherein the drain-drift region of the MOSFET is part of the base-region of the BJT, the device comprising:
  the semiconductor substrate of a first doping type;
  a first region of a second doping type, functioning as the buried layer within said substrate and located below the substrate surface;
  a second region of the first doping type, serving as the base of the BJT and drain-drift region of the MOSFET, and extending vertically from the substrate surface into said substrate to make contact to and create a semiconductor junction with the buried layer of the second doping type in said substrate;
  a third region of the second doping type that surrounds said second region of the first doping type and extends vertically from the substrate surface into said substrate to make an electrical contact to the buried layer of the second doping type and providing said third region with at least one ohmic contact;
  a dielectric film on said substrate surfaces of said second and third regions, at least one gate-electrode of a rectangular conducting stripe on said dielectric film, said stripe overlapping the interface between said second and third regions;
  at least a fourth region, of the second doping type extending into said second region serving as the emitter of the BJT, said fourth region being in a horizontal plane parallel with the interface between said second and third regions;
  a fifth region of said first doping type, extending into said third region that is adjacent to and slightly overlapped by the rectangular gate-electrode, serving as a source of the MOSFET;
  a sixth region of said second doping type, extending into said third region and providing ohmic contact to said third region; and
  a seventh region of said first doping type extending into a section of said second region and serving as the drain-drift region of the MOSFET, said seventh region being adjacent to and overlapped by said rectangular gate-electrode, wherein said seventh region simultaneously serves as the drain-drift region of the MOSFET and the base of the BJT.

13. The integrated sensor device according to claim 12, wherein an eighth region of said first doping type is formed in said second region, said eighth region being adjacent to said rectangular gate-electrode and an oxide isolation in said second region.

14. The integrated sensor device according to claim 12, wherein an eighth region of said second doping type is formed in said second region, making electrical contact to said buried layer of said second doping type, and forming a semiconductor junction with said second region, said eighth region being vertically separated from said fourth region.

15. The integrated sensor device according to claim 12, wherein gate-electrode structure of the MOSFET is formed around and above the second region of the first doping type that contains the emitter of the BJT.

16. The integrated sensor device according to claim 12, wherein said fourth region of the second doping type, is surrounded on all sides by an isolation oxide extending vertically from the substrate surface into said second region of the first doping type.

17. The integrated sensor device according to claim 12, wherein said first region of the second doping type and is vertically located 1.0 µm below the substrate surface.

18. The integrated sensor device according to claim 1, wherein said MOSFET is of n-type and said BJT is of pnp-type.

* * * * *